United States Patent
Lievens et al.

(10) Patent No.: US 9,656,071 B2
(45) Date of Patent: May 23, 2017

(54) CONTROL FOR HEARING PROSTHESIS FITTING

(71) Applicant: Cochlear Limited, Macquarie University (AU)

(72) Inventors: Stefan Lievens, Herent (BE); Thomas Stainsby, Mechelen (BE); Rami Banna, Paddington (AU); Christopher J. James, Toulouse (FR)

(73) Assignee: Cochlear Limited, Macquarie University (AU)

( * ) Notice: Subject to any disclaimer, the term of this patent is extended or adjusted under 35 U.S.C. 154(b) by 538 days.

(21) Appl. No.: 13/835,547

(22) Filed: Mar. 15, 2013

(65) Prior Publication Data

US 2014/0275730 A1   Sep. 18, 2014

(51) Int. Cl.
*H04R 25/00* (2006.01)
*A61N 1/36* (2006.01)

(52) U.S. Cl.
CPC ....... *A61N 1/36032* (2013.01); *H04R 25/606* (2013.01); *H04R 25/70* (2013.01)

(58) Field of Classification Search
CPC .................... H04R 25/70; A61N 1/36032
See application file for complete search history.

(56) References Cited

U.S. PATENT DOCUMENTS

| | | | |
|---|---|---|---|
| 7,650,005 B2 * | 1/2010 | Chalupper | H04R 25/70 381/312 |
| 8,244,365 B2 * | 8/2012 | Dijk | A61N 1/36032 600/559 |
| 2006/0287690 A1 | 12/2006 | Bouchataoui et al. | |
| 2007/0172088 A1 | 7/2007 | Olsen et al. | |
| 2011/0142272 A1 | 6/2011 | Takagi et al. | |
| 2012/0109006 A1 | 5/2012 | James et al. | |
| 2012/0215057 A1 | 8/2012 | Parker | |
| 2012/0290045 A1 | 11/2012 | Nicolai et al. | |

FOREIGN PATENT DOCUMENTS

KR   1020090065793 A1   6/2009

OTHER PUBLICATIONS

International Preliminary Report on Patentability and Written Opinion for PCT/IB2014/059622 dated Sep. 24, 2015.

* cited by examiner

*Primary Examiner* — Mark W Bockelman
(74) *Attorney, Agent, or Firm* — McDonnell Bochnen Hulbert & Berghoff LLP

(57) ABSTRACT

A method for adjusting parameters of a hearing prosthesis system includes adjusting a control to shift an audiogram associated with a first stimulator, applying a prescription rule using the shifted audiogram to adjust a cross-over frequency that defines a first frequency range and a second frequency range. The first stimulator is configured to apply stimulation signals in the first frequency range and a second stimulator is configured to apply stimulation signals in the second frequency range. The method also includes applying the prescription rule using the shifted audiogram to determine gain and maximum power output (MPO) levels for the first frequency range associated with the first stimulator.

16 Claims, 3 Drawing Sheets

CONTROL FOR HEARING PROSTHESIS FITTING

BACKGROUND

Various types of hearing prostheses provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound directly or indirectly to a person's bone or teeth, thereby causing vibrations in the person's inner ear and bypassing the person's auditory canal and middle ear.

Vibration-based hearing devices include, for example, bone anchored devices, direct acoustic cochlear stimulation devices, or other vibration-based devices. A bone-anchored device typically utilizes a surgically implanted mechanism or a passive connection through the skin or teeth to transmit vibrations corresponding to sound via the skull. A direct acoustic cochlear stimulation device also typically utilizes a surgically implanted mechanism to transmit vibrations corresponding to sound, but bypasses the skull and more directly stimulates the inner ear. Other non-surgical vibration-based hearing devices may use similar vibration mechanisms to transmit sound via direct or indirect vibration of teeth or other cranial or facial bones or structures.

Persons with certain forms of sensorineural hearing loss may benefit from hearing prostheses, such as cochlear implants and/or auditory brainstem implants. For example, cochlear implants can provide a person having sensorineural hearing loss with the ability to perceive sound by stimulating the person's auditory nerve via an array of electrodes implanted in the person's cochlea. A microphone of the cochlear implant detects sound waves, which are converted into a series of electrical stimulation signals that are delivered to the implant recipient's cochlea via the array of electrodes. Auditory brainstem implants can use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound.

Further, some persons may benefit from hearing prostheses that combine one or more characteristics of the acoustic hearing aids, vibration-based hearing devices, cochlear implants, and auditory brainstem implants to enable the person to perceive sound. Such hearing prostheses can be referred to generally as bimodal hearing prostheses. Generally, the term bimodal means more than one stimulation mode, and not necessarily only two stimulation modes.

The effectiveness of any of the above-described prostheses depends not only on the design of the prosthesis itself but also on how well the prosthesis is configured for or "fitted" to a prosthesis recipient. The fitting of the prosthesis, sometimes also referred to as "programming" or "mapping," creates a set of configuration settings or parameters and other data that define the specific characteristics of the stimulation signals (e.g., sound or acoustic stimulation signals, vibration or mechanical stimulation signals, or electrical stimulation signals) delivered to the relevant portions of the person's outer ear, middle ear, inner ear, auditory nerve, brain stem, etc. This configuration information is sometimes referred to as the recipient's "program" or "MAP."

One aspect of hearing prosthesis fitting or programming includes setting values for each channel or frequency band of a normal hearing range. Two of these values are often referred to as the threshold level (also commonly referred to as the "THR" or "T level") and the maximum comfort level (also commonly referred to as the "Most Comfortable Loudness level," "MCL," "M level," "C level," "Maximum Comfortable Loudness," or simply "comfort level"). Threshold levels are comparable to acoustic threshold levels and comfort levels indicate the level at which a perceived sound is loud but comfortable.

Typically, an audiologist or clinician uses a hearing prosthesis fitting system that includes interactive software and computer hardware to create individualized recipient map data, including the settings for threshold and comfort levels. The audiologist or clinician can control the fitting system to carry out one or more of the functions of mapping, neural response measuring, acoustic stimulating, and/or recording of neural response measurements and other stimuli. More recent advances allow prosthesis recipients to program the hearing prosthesis themselves or surgeons to create initial MAPs upon implantation that can then be adjusted by the recipient.

SUMMARY

The present disclosure relates to fitting or adjusting parameters of a hearing prosthesis for a recipient. The hearing prosthesis can be a bimodal hearing prosthesis that is configured to apply more than one form of stimulation, such as acoustic, mechanical, or electrical, to a prosthesis recipient. Illustratively, the bimodal hearing prosthesis can include electrical stimulation components, such as cochlear implant or auditory brainstem implant components, and acoustic stimulation or mechanical stimulation components, such as acoustic hearing aid or vibration-based hearing device components, respectively.

In one example, fitting of a bimodal hearing prosthesis includes shifting a hearing prosthesis recipient's audiogram that corresponds to particular stimulation components, such as acoustic stimulation components. A prescription rule is applied to the shifted audiogram to determine configuration settings for the corresponding stimulation components and to set a cross-over frequency between the plurality of stimulation components, such as between acoustic stimulation components and electrical stimulation components.

Various aspects are described herein as being implemented by methods, systems (such as, a hearing prosthesis and/or a separate computing device (e.g., remote control) for adjusting parameters of the hearing prosthesis), and/or programming in the form of a non-transitory computer-readable medium.

DETAILED DESCRIPTION

Figure 1:
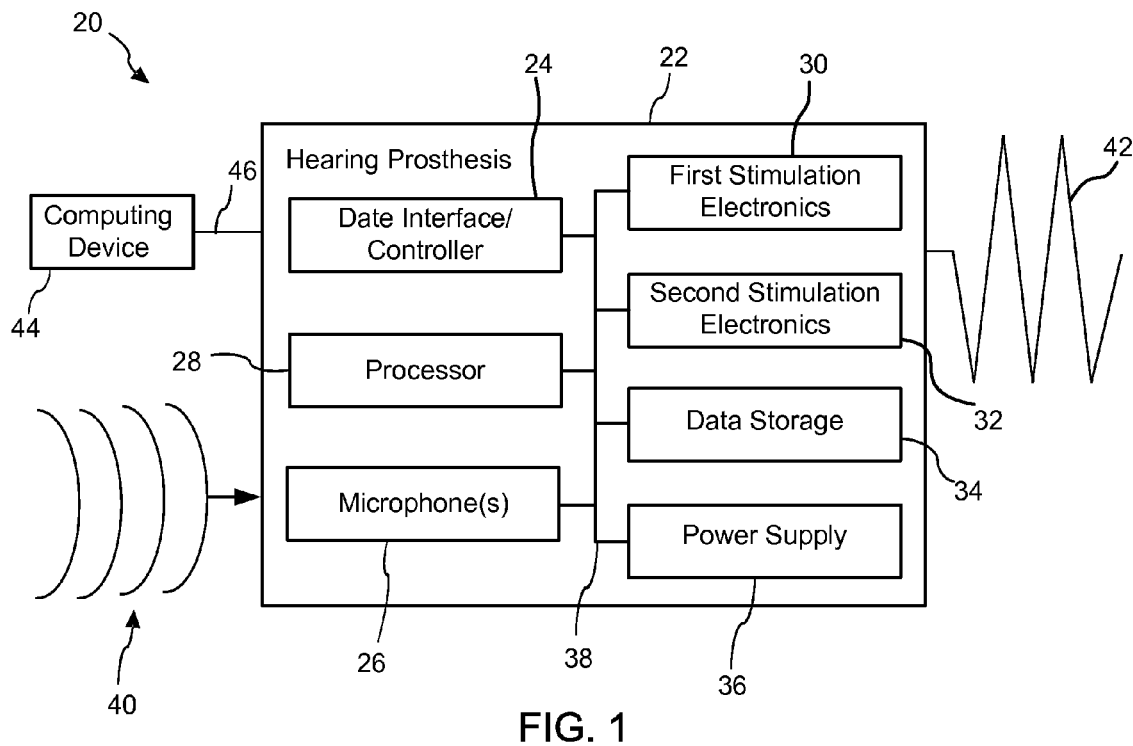
FIG. 1 illustrates a block diagram of a hearing prosthesis system according to an embodiment of the present disclosure.

The following detailed description describes various features, functions, and attributes with reference to the accompanying figures. In the figures, similar symbols typically identify similar components, unless context dictates otherwise. The illustrative embodiments described herein are not meant to be limiting. Certain features, functions, and attributes disclosed herein can be arranged and combined in a variety of different configurations, all of which are contemplated in the present disclosure.

For illustration purposes, various examples are described herein with respect to a bimodal electro-acoustic hearing prosthesis that includes electrical stimulation components and acoustic stimulation components. However, various features and functions disclosed herein are also applicable to other types of bimodal or single mode hearing prostheses. One example of a bimodal electro-acoustic hearing prosthesis includes cochlear implant components that provide electrical stimulation and acoustic hearing aid components that provide acoustic stimulation.

A typical recipient of such an electro-acoustic hearing prosthesis generally has sensorineural hearing loss that affects a higher frequency range more severely and may maintain some useful lower frequency range hearing. Thus, in the present example, the electro-acoustic hearing prosthesis includes cochlear implant components to deliver sound through electrical stimulation signals for the higher frequency range and acoustic hearing aid components to deliver sound through acoustic stimulation signals for the lower frequency range.

Generally, the fitting and adjustment of such a bimodal hearing prosthesis is carried out using two fitting protocols. A first protocol is used for fitting the electrical stimulation and a second protocol is used for the acoustic stimulation. In one example, the first protocol is used for fitting cochlear implant components and includes measuring threshold levels and maximum comfort levels for a plurality of electrodes across a cochlear electrode array and interpolating the threshold and maximum comfort levels for the other electrodes. These threshold and maximum comfort levels are used to define the recipient's electrical hearing range and this electrical hearing range is used by configuration settings, such as a speech algorithm, to convert external acoustic signals into electrical stimulation signals that are applied to the recipient to allow the recipient to perceive the acoustic signals as sound.

In this example, the second protocol is used for fitting acoustic hearing aid components. For instance, this fitting process includes measuring threshold levels and maximum comfort levels for a plurality of frequency channels of the acoustic hearing aid components and interpolating the threshold and maximum comfort levels for other frequency channels. The threshold levels are used to define an audiogram for the recipient's residual hearing. Generally, the audiogram is a graph of the audible thresholds for a range of frequencies. The fitting process then applies a prescription rule to the audiogram and the maximum comfort levels to define parameters for the acoustic hearing aid components. These parameters include, for example, gain settings and maximum power output (MPO) levels across the range of frequencies. These gain settings and MPO levels can then be used to amplify or otherwise process external acoustic signals into acoustic stimulation signals that are applied to the recipient to allow the recipient to perceive the external acoustic signals as sound in a normal hearing range.

These first and second protocols and other fitting processes (such as further fine-tuning, balancing, and determining a cross-over frequency between the electrical stimulation and the acoustic stimulation) can be carried out by a clinician making a series of psychophysical tests on separate acoustic and electrical stimulation systems. Once the separate acoustic and electrical stimulation systems are fitted, a user, such as the clinician, the hearing prosthesis recipient, or some other third-party, can adjust the fitting using, for example, a remote control that is designed with a user interface having controls for adjusting the various parameters of the hearing prosthesis.

Illustratively, one such remote control for a hearing prosthesis with a single stimulation mode, such as a cochlear implant, is designed with a user interface that abstracts a number of hearing prosthesis settings or parameter values and provides a limited set of controls for a user to adjust the parameter values. In this example, the remote control includes a master volume control to adjust levels across all frequency channels, a bass control to adjust levels for lower frequency channels, and a treble control to adjust levels for higher frequency channels.

One example of the present disclosure expands on the functionality of this remote control design and user interface to adjust the fitting of a bimodal hearing prosthesis (rather than a cochlear implant or other hearing prosthesis that is configured to deliver a single form of stimulation). In the illustrative bimodal hearing prosthesis that includes acoustic stimulation components and electrical stimulation components, generally, a first range of frequency channels are assigned to the acoustic stimulation components and a second range of frequency channels are assigned to the electrical stimulation components. Together, the first and second ranges of frequency channels characterize a frequency range of normal human hearing. Further, a cross-over frequency between the first and second frequency ranges defines where stimulation changes from acoustic to electrical.

In this example, an acoustic stimulation control is used to adjust all of the parameters for acoustic stimulation at once. More particularly, adjusting the acoustic stimulation control up or down causes corresponding up or down linear shifts in the recipient's audiogram. The hearing prosthesis and/or remote control can then apply a prescription rule to the shifted audiogram to adjust parameters for the acoustic stimulation components, such as the gain and MPO parameters. This shift of the audiogram and application of the prescription rule also adjusts the cross-over frequency between the acoustic and electrical stimulation.

Further, in this example, a first electrical stimulation control is used to adjust levels across all frequency channels associated with electrical stimulation and a second electrical stimulation control is used to adjust levels for higher frequency channels associated with electrical stimulation. For example, the higher frequency channels can be defined as a percentage of the electrical stimulation range, such as an upper 40% of frequencies in the electrical stimulation range. Generally, adjusting the first and second controls adjusts comfort levels and/or threshold levels for the electrical stimulation.

Generally, as disclosed herein, providing the acoustic stimulation control and one dimension of change (e.g., adjusting a single control up or down) to adjust all of the parameters for acoustic stimulation can simplify the fitting procedure. Additionally, examples described herein of dynamically adjusting a cross-over frequency between acoustic and electrical stimulation can reduce potential user errors that might otherwise be made to fine tune the cross-over frequency and other parameters that affect channels around the cross-over frequency range.

Referring now to FIG. 1, an example hearing prosthesis system 20 includes a bimodal hearing prosthesis 22. In the present example, the bimodal hearing prosthesis 22 includes components to apply more than one form of stimulation. For instance, the bimodal hearing prosthesis 22 can include components of a cochlear implant, an acoustic hearing aid, a bone-anchored device, a direct acoustic cochlear stimulation device, an auditory brainstem implant, or any other type of hearing prosthesis configured to assist a prosthesis recipient in perceiving sound.

The hearing prosthesis 22 illustrated in FIG. 1 includes a data interface or controller 24 (such as a universal serial bus (USB) controller), one or more microphones 26, one or more processors 28 (such as digital signal processors (DSPs)), first stimulation electronics 30, second stimulation electronics 32, data storage 34, and a power supply 36 all of which are illustrated as being coupled directly or indirectly via a wired or wireless link 38. In one non-limiting example, the first stimulation electronics 30 include acoustic stimulation electronics, such as hearing aid components, for providing acoustic stimulation to a recipient and the second stimulation electronics 32 include electrical stimulation electronics, such as cochlear implant components, for providing electrical stimulation to the recipient.

Generally, the microphone(s) 26 are configured to receive external acoustic signals 40. The microphone(s) 26 can include combinations of one or more omnidirectional or directional microphones that are configured to receive background sounds and/or to focus on sounds from a specific direction, such as generally in front of the prosthesis recipient. Alternatively or in conjunction, the hearing prosthesis 22 is configured to receive sound information from other sources, such as sound information received through the controller 24 from an external source.

The processor 28 is configured to process, amplify, encode, or otherwise convert the acoustic signals 40 into stimulation data that are provided to the acoustic and electrical stimulation electronics 30, 32. The acoustic and electrical stimulation electronics 30, 32 can then apply the stimulation data to the recipient as output stimulation signals 42 to allow the recipient to perceive the original external acoustic signals 40 as sound. More particularly, in the context of the present bimodal hearing prosthesis 22, the acoustic signals 40 are converted into acoustic stimulation data and electrical stimulation data. The acoustic stimulation data are provided to the acoustic stimulation electronics 30 to apply acoustic output stimulation signals 42 to the recipient. The electrical stimulation data are provided to the electrical stimulation electronics 32 to apply electrical output stimulation signals 42 to the recipient.

The processor 28 converts the external acoustic signals 40 into the stimulation data in accordance with configuration settings or data for a prosthesis recipient. Generally, the configuration settings allow a hearing prosthesis to be configured for or fitted to a particular recipient. More particularly, in the present example, the bimodal hearing prosthesis 22 can be programmed with configuration settings that include acoustic stimulation configuration settings for generating the acoustic stimulation data and electrical stimulation configuration settings for generating the electrical stimulation data. These configuration settings can be stored in the data storage 34.

Illustratively, the electrical stimulation configuration settings include speech algorithms that are implemented by the processor 28 to generate the electrical stimulation data from the acoustic signals 40. For electrical stimulation data that are applied to cochlear implant components and, more particularly, to a cochlear electrode array implanted in a recipient, the stimulation data can define one or more of an intended electrode, mode of stimulation, stimulation amplitude, and stimulation duration. Thus, the electrical stimulation data can be used to control the timing and intensity of auditory stimulation pulses that are applied to a recipient by the stimulation electronics 32.

Generally, speech algorithms include, but are not limited to, Continuous Interleaved Sampling (CIS), Spectral PEAK Extraction (SPEAK), Advanced Combination Encoders (ACE), Fundamental Asynchronous Stimulus Timing (FAST), Simultaneous Analog Stimulation, MPS, Paired Pulsatile Sampler, Quadruple Pulsatile Sampler, Hybrid Analog Pulsatile, n-of-m, and HiRes. More particularly, SPEAK is a low rate strategy that can operate within the 250-500 Hz range, ACE is a combination of CIS and SPEAK, and FAST is a low-rate, asynchronous stimulation that is temporally locked to envelope peaks of the input. Other proprietary and non-proprietary speech algorithms are also possible. The operation of these algorithms provides information on a stimulation mode (e.g., monopolar or bipolar electrode), a target electrode(s), and an amplitude of stimulation pulse(s), for example.

Referring again to the acoustic stimulation configuration settings, these settings include prescription rules for defining parameters, such as gain and MPO levels or settings, from the hearing prosthesis recipient's audiogram and maximum comfort levels across a range of frequencies for acoustic stimulation. As discussed above, the audiogram is a graph of the audible thresholds for a range of frequencies. In some cases, the audiogram is defined by measured threshold levels across the recipient's residual hearing range. If a recipient specific audiogram is unavailable, a population average audiogram can also be used with the prescription rule to fit acoustic hearing aid components of the bimodal hearing prosthesis 22. In the present example, the prescription rule can also be applied to the audiogram to set a cross-over frequency between the acoustic stimulation and the electrical stimulation.

Generally, prescription rules are mathematical models or algorithms for calculating optimal gain settings so that external sounds are perceived by a hearing prosthesis recipient intelligibly and at similar loudness that the external sounds would be perceived by a normal-hearing person.

Prescription rules typically focus on making speech intelligible and reducing background noise. Some prescription rules are non-linear and apply different gain settings for different frequencies or frequency bands to provide a more fine-tuned hearing prosthesis fitting for the recipient. Example prescription rules include, but are not limited to, National Acoustic Laboratories' (NAL) prescriptions rules (including NAL-R, NAL-RP, NAL-NL2, etc.), the Desired Sensation Level (DSL) prescription rule, and the Cochlear Hybrid Prescription Rule (CHP). Other proprietary and non-proprietary prescription rules are also possible.

As discussed generally above, the first stimulation electronics 30 can include hearing aid components, such as a small speaker or earphone, and the second stimulation electronics 32 can include cochlear implant components, such as a cochlea electrode array. In other examples, the stimulation electronics 30, 32 can include other types of hearing prosthesis components, such as an auditory nerve stimulator to transmit sound via direct mechanical stimulation, an auditory vibrator to transmit sound via direct bone vibrations, auditory nerve electrode arrays, and the like.

Referring back to the power supply 36, this power supply provides power to various components of the hearing prosthesis 22. The power supply 36 can be any suitable power supply, such as non-rechargeable or rechargeable batteries. In one example, the power supply 36 is a battery that can be recharged wirelessly, such as through inductive charging. Such a wirelessly rechargeable battery facilitates complete subcutaneous implantation of the prosthesis 22 to provide a fully or at least partially implantable prosthesis. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined, or otherwise, associated with use of the prosthesis.

Referring again to the data storage 34, this component generally includes any suitable volatile and/or non-volatile storage components. Further, the data storage 34 may include computer-readable program instructions and perhaps additional data. In some embodiments, the data storage 34 stores data and instructions used to perform at least part of the herein-described methods and processes and/or at least part of the functionality of the systems described herein. Although, the data storage 34 in FIG. 1 is illustrated as a separate block, in some embodiments, the data storage can be incorporated into other components of the prosthesis 22, such as the processor 28.

The system 20 illustrated in FIG. 1 further includes a computing device 44 that is configured to be communicatively coupled to the hearing prosthesis 22 via a connection or link 46. The link 46 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, inductive or electromagnetic coupling or link, and the like.

In general, the computing device 44 and the link 46 are used to operate the hearing prosthesis 22 in various modes. In one example, the computing device 44 and the link 46 are used to adjust various parameters of the bimodal hearing prosthesis 22. The computing device 44 and the link 46 can also be used to load a recipient's configuration settings on the hearing prosthesis 22 such as via the data interface 24. In another example, the computing device 44 and the link 46 are used to upload other program instructions and firmware upgrades to the hearing prosthesis 22. In yet other examples, the computing device 44 and the link 46 are used to deliver data (e.g., sound information) and/or power to the hearing prosthesis 22 to operate the components thereof and/or to charge the power supply 36. Still further, various other modes of operation of the prosthesis 22 can be implemented by utilizing the computing device 44 and the link 46.

The computing device 44 can further include various additional components, such as a processor and a power source. Further, the computing device 44 can include user interface or input/output devices, such as buttons, dials, a touch screen with a graphic user interface, and the like, that can be used to turn the prosthesis 22 on and off, adjust the volume, adjust or fine tune the configuration data or parameters, etc. Thus, the computing device 44 can be utilized by the recipient or a third party, such as a guardian of a minor recipient or a health care professional, to control or adjust the hearing prosthesis 22.

Various modifications can be made to the system 20 illustrated in FIG. 1. For example, user interface or input/output devices can be incorporated into the hearing prosthesis 22, instead of or in combination with the user interface or input/output devices of the computing device 44. Further, the system 20 may include additional or fewer components arranged in any suitable manner. In some examples, the system 20 may include other components to process external audio signals, such as components that measure vibrations in the skull caused by audio signals and/or components that measure electrical outputs of portions of a person's hearing system in response to audio signals.

Additionally, depending on the type and design of the system 20, the illustrated components may be enclosed within a single operational unit or distributed across multiple operational units, for example, two or more internal units or an external unit and an internal unit. Generally, an internal unit can be hermetically sealed and adapted to be at least partially implanted in a recipient.

Figure 2:
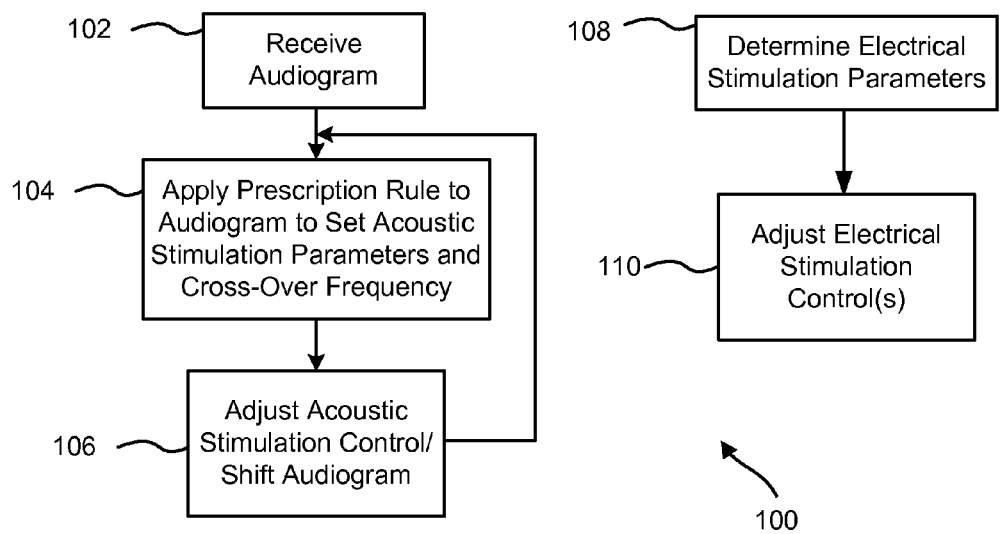
FIG. 2 is a flowchart showing a method or algorithm for fitting a bimodal hearing prosthesis.

Referring now to FIG. 2, example methods 100 are illustrated, which can be implemented by the systems and devices described hereinabove. Generally, the method 100 may include one or more operations, functions, or actions as illustrated by one or more of blocks 102-110. Although the blocks 102-106 and the blocks 108-110 are illustrated in sequential order, respectively, and in parallel, these sets of blocks may also be performed in series and/or in a different order than illustrated.

In addition, each block 102-110 may represent a module, a segment, or a portion of program code, which includes one or more instructions executable by a processor for implementing specific logical functions or steps in the process. The program code may be stored on any type of computer readable medium or storage device including a disk or hard drive, for example. The computer readable medium may include non-transitory computer readable medium, such as computer-readable media that stores data for short periods of time like register memory, processor cache, and Random Access Memory (RAM). The computer readable medium may also include non-transitory media, such as secondary or persistent long term storage, like read only memory (ROM), optical or magnetic disks, compact-disc read only memory (CD-ROM), etc. The computer readable media may also include any other volatile or non-volatile storage systems. The computer readable medium may be considered a computer readable storage medium, for example, or a tangible storage device. In addition, one or more of the blocks 102-110 may represent circuitry that is wired to perform the specific logical functions of the method 100.

Figure 3:
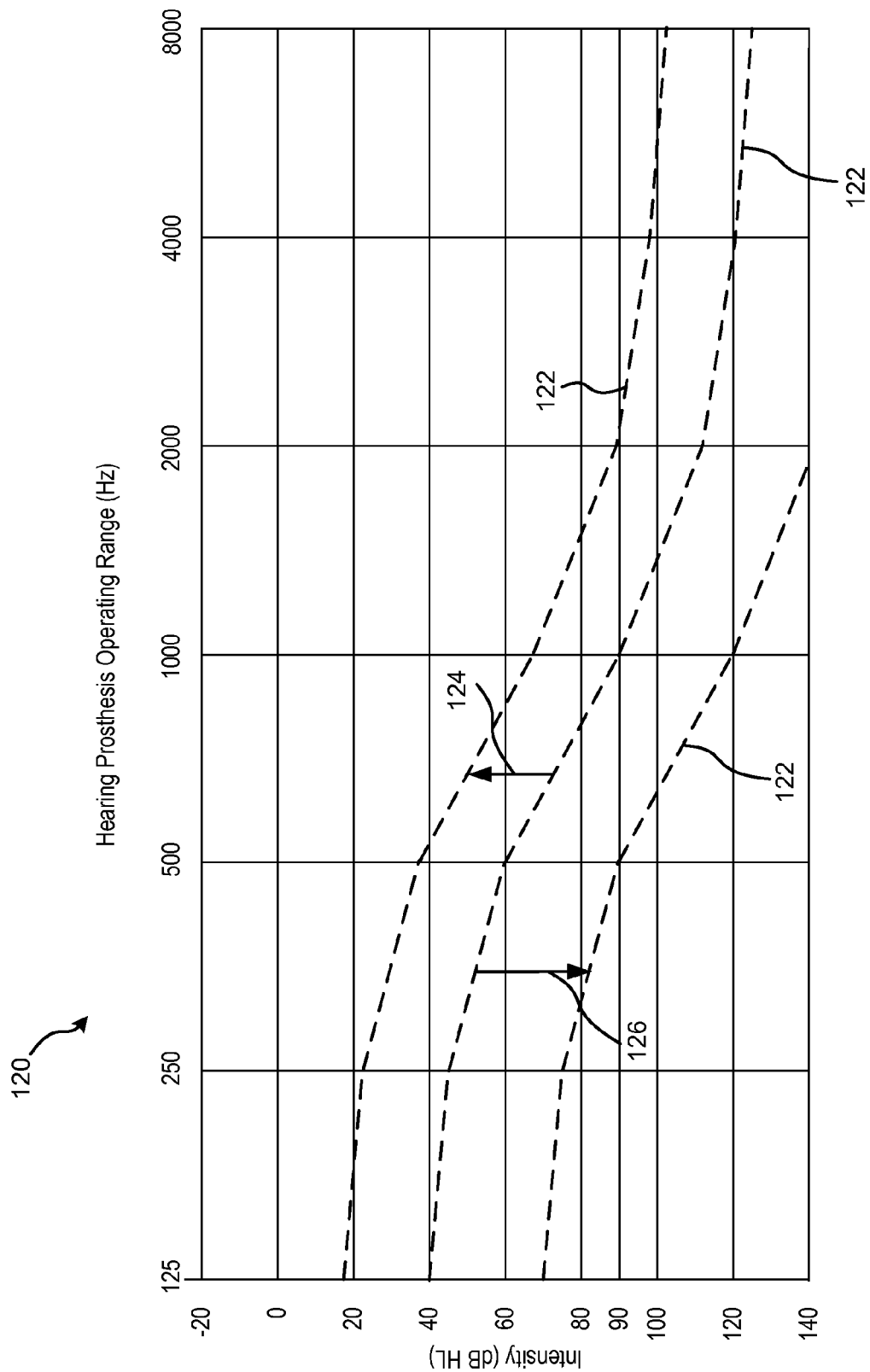
FIG. 3 is a graph of an example audiogram for a hearing prosthesis recipient.

In FIG. 2, at block 102, a device, such as the hearing prosthesis 22, the computing device 44, or some other computing device, receives an audiogram for a hearing prosthesis recipient. This audiogram can be defined based on measured hearing threshold values for a particular recipient or can be a population average audiogram. FIG. 3 illustrates an example audiogram 120 that can be used to fit a hearing prosthesis. In the audiogram 120, a line 122 shows a recipient's hearing loss in decibels as a function of acoustic frequency (dB HL) between about 125 Hz and 8 kHz. The hearing loss represented by the audiogram line 122 of FIG. 3 is sometimes referred to as a ski-sloped hearing loss, which generally corresponds to a recipient with some residual low frequency hearing with relatively severe hearing loss at higher frequencies.

At block 104, the device applies a prescription rule to the received audiogram (and perhaps other data, e.g., maximum comfort levels) to set parameters for the acoustic stimulation components of the hearing prosthesis. Generally, the prescription rule defines gain and MPO levels based on the audiogram such that incoming external audio signals are amplified to a comfortable hearing range for the recipient. The application of the prescription rule also sets the cross-over frequency between the acoustic stimulation (lower frequency range) and electrical stimulation (higher frequency range). Illustratively, the cross-over frequency can be set to the frequency (or set to the next closest frequency channel) where the audiogram crosses a threshold hearing loss level between acoustic stimulation and electrical stimulation. In FIG. 3, an example threshold hearing loss level is 90 dB HL and the corresponding cross-over frequency of the audiogram line 122 in the present example is about 1 kHz. At block 104, once the cross-over frequency is determined, electrical stimulation for frequencies below the cut-off frequency can be disabled.

At block 106, a user, such as a clinician, the hearing prosthesis recipient, or some other party, adjusts an acoustic stimulation control to modify the acoustic stimulation parameters. Adjusting the acoustic stimulation control up or down corresponds to a linear shift in the audiogram. More particularly, referring to FIG. 3, adjusting the acoustic stimulation control up will shift the audiogram line 122 down, which corresponds to a greater hearing loss, and adjusting the acoustic stimulation control down will shift the audiogram line up, which corresponds to a lesser hearing loss. FIG. 3 illustrates an example adjustment of the acoustic stimulation control down and a corresponding upward shift 124 of the audiogram line 122. FIG. 3 also illustrates another example adjustment of the acoustic stimulation control up and a corresponding downward shift 126 of the audiogram line 122.

Thereafter, control passes back to block 104, and the device applies the prescription rule to the shifted audiogram to set (reset) the parameters for the acoustic stimulation and to dynamically adjust the cross-over frequency. In the example shown in FIG. 3, the upward shift 124 of the audiogram line 122 sets a new cross-over frequency (with the threshold loss level at 90 dB HL) at about 2 kHz. Further, as shown in FIG. 3 the downward shift 126 of the audiogram line 122 sets a new cross-over frequency (with the threshold loss level at 90 dB HL) at about 500 Hz.

Referring now to block 108, the device determines the electrical stimulation parameters through a fitting process or protocol. For example, the fitting process may include a clinician using a fitting system to measure recipient responses to electrical stimulation signals to determine threshold and comfort levels for a plurality of frequencies above the cross-over frequency. These threshold and comfort levels can then be used to set other electrical stimulation parameters. At block 110, a user can adjust one or more electrical stimulation controls to modify the electrical stimulation parameters. For example, a first electrical stimulation control can be used to modify electrical stimulation parameters across all frequency channels associated with electrical stimulation and a second electrical stimulation control can be used to modify electrical stimulation parameters for higher frequency channels associated with electrical stimulation.

In one illustrative example, the acoustic stimulation and electrical stimulation controls can be included as part of a single user interface. This user interface for fitting a bimodal hearing prosthesis can include one or more acoustic stimulation controls and one or more electrical stimulation controls. More particularly, in one example, the user interface includes an acoustic stimulation control to adjust parameters for the acoustic stimulation (e.g., shift the recipient's audiogram) and to dynamically adjust the cross-over frequency. In this example, the user interface can also include a first electrical stimulation control that functions to adjust all levels for the electrical stimulation and a second electrical stimulation control that functions to adjust levels for a high frequency range of the electrical stimulation. In other examples, the user interface controls can be mapped to different functions and/or the user interface can include additional controls for fine-tuning or balancing the parameters of the hearing prosthesis.

Figure 4:
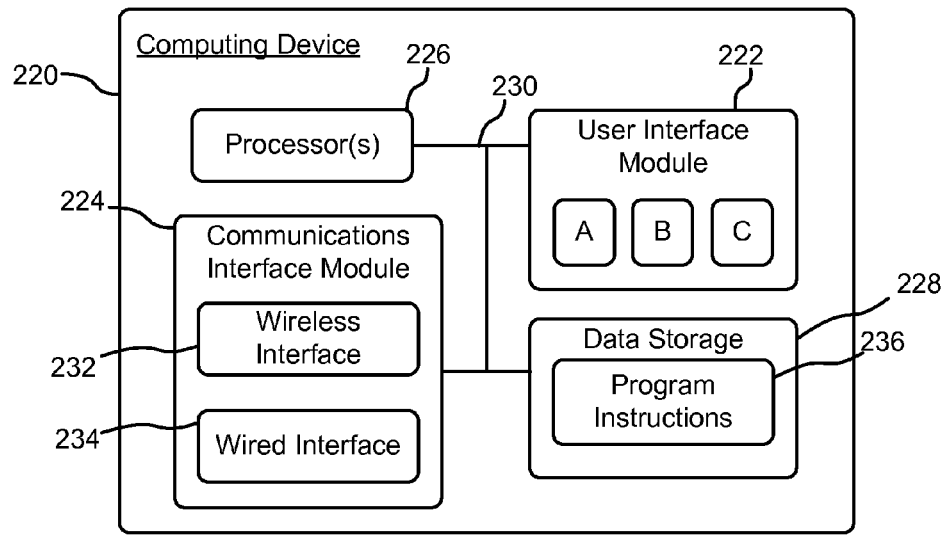
FIG. 4 illustrates a block diagram of a computing device according to an embodiment that can be used to implement aspects of the present disclosure.

Referring now to FIG. 4, a computing device 220 is illustrated, which may be the same or different from the computing device 44 of FIG. 1. Generally, the computing devices 44, 220 can be used to implement aspects of various embodiments of the disclosed systems, methods, and articles of manufacture. For example, the computing devices 44, 220 can provide a remote control device for adjusting various parameters of a hearing prosthesis.

In FIG. 4, the computing device 220 includes a user interface module 222, a communications interface module 224, one or more processors 226, and data storage 228, all of which are linked together via a system bus or other connection mechanism 230. The user interface module 222 includes user input/output devices such as a keyboard, a keypad, a touch screen, a computer mouse, a track ball, a joystick, and/or other similar devices, now known or later developed. In one example, the user interface module 222 provides three controls A, B, and C, which, in the context of a cochlear implant, can correspond to a first acoustic stimulation control, a first electrical stimulation control, and a second electrical stimulation control, among other possibilities. In the context of the bimodal hearing prosthesis described herein, the controls A, B, C can correspond to an acoustic stimulation control, a first electrical stimulation control, and a second electrical stimulation control.

Additionally, the user interface module 222 is also configurable to provide outputs to user display devices, such as one or more cathode ray tubes (CRTs), liquid crystal displays (LCDs), light emitting diodes (LEDs), displays using digital light processing (DLP) technology, printers, light bulbs, and/or other similar devices, now known or later developed. The user interface module 222 may also be configured to generate audible output(s), such as a speaker, speaker jack, audio output port, audio output device, earphones, and/or other similar devices, now known or later developed.

The communications interface module 224 includes one or more wireless interfaces 232 and/or wired interfaces 234 configured to send and receive data to and/or from other devices and systems (e.g., a hearing prosthesis) via a communications link (e.g., the connection 44 of FIG. 1). The wireless interfaces 232 may include one or more wireless transceivers, such as a Bluetooth transceiver, a Wi-Fi transceiver, a WiMAX transceiver, electromagnetic inductive link transceiver, and/or other similar types of wireless transceiver configurable to communicate via a wireless protocol. The wired interfaces 234 may include one or more wired transceivers, such as an Ethernet transceiver, a Universal Serial Bus (USB) transceiver, or similar transceiver configurable to communicate via a twisted pair wire, a coaxial cable, a fiber-optic link, or a similar physical connection.

The one or more processors 226 may include one or more general purpose processors, such as microprocessors manufactured by Intel, Apple, Advanced Micro Devices, etc., and/or one or more special purpose processors, such as digital signal processors, application specific integrated circuits, etc. The one or more processors 226 are configured to execute computer readable program instructions 236 stored in the data storage 228, such as instructions to perform aspects of the method 100 of FIG. 2.

The data storage 228 includes one or more computer readable storage media that can be read or accessed by at least one of the processors 226. The one or more computer-readable storage media includes volatile and/or non-volatile storage components, such as optical, magnetic, organic, or other memory or disc storage, which can be integrated in whole or in part with at least one of the processors 226. In some embodiments, the data storage 228 is implemented using a single physical device, such as one optical, magnetic, organic or other memory, or disc storage unit, while in other embodiments, the data storage is implemented using two or more physical devices. In the present example, the data storage 228 includes the computer readable program instructions 236 and perhaps additional data. In some embodiments, the data storage 228 includes storage required to perform at least some aspects of the method of FIG. 2.

In some embodiments, the disclosed features and functions of the systems and methods shown and described herein may be implemented as computer program instructions encoded on computer-readable media in a machine-readable format.

Figure 5:
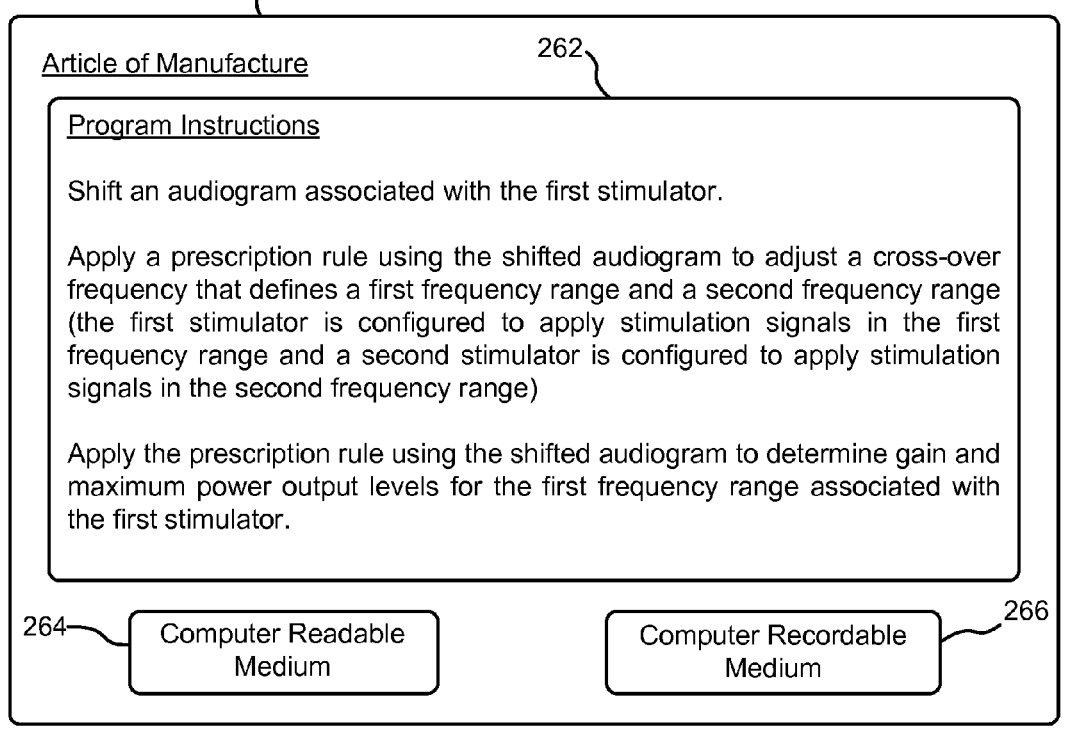
FIG. 5 is a block diagram of an article of manufacture including computer-readable media with instructions for fitting a bimodal hearing prosthesis.

FIG. 5 shows an example of an article of manufacture 260 including computer readable media with instructions 262 for adjusting parameters of a bimodal hearing prosthesis. In FIG. 5, the example article of manufacture 260 includes computer program instructions 262 for executing a computer process on a computing device, arranged according to at least some embodiments described herein.

In some examples, the article of manufacture 260 includes a computer-readable medium 264, such as, but not limited to, a hard disk drive, a Compact Disc (CD), a Digital Video Disk (DVD), a digital tape, flash memory, etc. In some implementations, the article of manufacture 260 includes a computer recordable medium 266, such as, but not limited to, a hard disk drive, a Compact Disc (CD), a Digital Video Disk (DVD), a digital tape, flash memory, etc. The one or more programming instructions 262 include, for example, computer executable and/or logic implemented instructions. In some embodiments, a computing device such as the processor 28, the computing device 44, and/or the computing device 220, alone or in combination with one or more additional processors or computing devices, may be configured to perform certain operations, functions, or actions to implement the features and functionality of the disclosed systems and methods based at least in part on the programming instructions 262.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A method for adjusting parameters of a hearing prosthesis system that includes a first stimulator, a second stimulator, and a processor, the method comprising:
   adjusting a control to shift an audiogram associated with the first stimulator;
   applying, by the processor, a prescription rule using the shifted audiogram to adjust a cross-over frequency between a first frequency range and a second frequency range, wherein the first stimulator is configured to apply stimulation signals in the first frequency range and the second stimulator is configured to apply stimulation signals in the second frequency range, and wherein the cross-over frequency between the first frequency range and second frequency range defines where stimulation changes from the first stimulator to the second stimulator;
   disabling the second stimulator from applying stimulation signals at frequencies below the adjusted cross-over frequency; and
   applying, by the processor, the prescription rule using the shifted audiogram to determine gain and maximum power output levels for the first frequency range associated with the first stimulator.

2. The method of claim 1, wherein the first stimulator includes an acoustic stimulator and the second stimulator includes an electrical stimulator.

3. The method of claim 2, wherein the electrical stimulator includes a cochlea electrode array.

4. The method of claim 1, wherein the audiogram is a population average audiogram.

5. The method of claim 1, wherein the first frequency range is lower than the second frequency range.

6. The method of claim 1, further comprising adjusting a second control to adjust gain and MPO levels for the second frequency range associated with the second stimulator.

7. The method of claim 1, wherein the adjusted cross-over frequency corresponds to a frequency at which the shifted audiogram crosses a threshold level.

8. A bimodal hearing prosthesis, comprising:
   first stimulation electronics configured to apply first stimulation signals in a first frequency range;
   second stimulation electronics configured to apply second stimulation signals in a second frequency range; and
   a processor configured to
      receive a shifted audiogram;
      apply a prescription rule using the shifted audiogram to adjust a cross-over frequency between the first and second frequency ranges that defines where stimulation changes from using the first stimulation electronics to using the second stimulation electronics;
      disable the second stimulation electronics from applying the second stimulation signals at frequencies below the adjusted cross-over frequency; and
      apply the prescription rule using the shifted audiogram to calculate parameters for the first frequency range associated with the first stimulation electronics.

9. The bimodal hearing prosthesis of claim 8, wherein the parameters include gain and maximum power output levels.

10. The bimodal hearing prosthesis of claim 8, wherein the first stimulation electronics include an acoustic stimulator and the second stimulation electronics include an electrical stimulator.

11. The bimodal hearing prosthesis of claim 10, wherein the electrical stimulator includes a cochlea electrode array.

12. The bimodal hearing prosthesis of claim 8, wherein the audiogram is a population average audiogram.

13. The bimodal hearing prosthesis of claim 8, wherein the processor is further configured to receive instructions to linearly shift the audiogram up or down, and to apply the prescription rule to the shifted audiogram.

14. The bimodal hearing prosthesis of claim 8, wherein the first frequency range is lower than the second frequency range.

15. The bimodal hearing prosthesis of claim 8, wherein the processor is further configured to receive instructions to adjust parameters for the second frequency range associated with the second stimulation electronics.

16. The bimodal hearing prosthesis of claim 8, wherein the adjusted cross-over frequency corresponds to a frequency at which the shifted audiogram crosses a threshold level.

\* \* \* \* \*